US007094805B2

(12) United States Patent
Danishefsky et al.

(10) Patent No.: US 7,094,805 B2
(45) Date of Patent: Aug. 22, 2006

(54) TOTAL SYNTHESIS OF MERRILACTONE A

(75) Inventors: Samuel J. Danishefsky, Englewood, NJ (US); Vladimir B. Birman, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/318,777

(22) Filed: Dec. 13, 2002

(65) Prior Publication Data
US 2004/0006121 A1 Jan. 8, 2004

Related U.S. Application Data

(60) Provisional application No. 60/340,449, filed on Dec. 14, 2001.

(51) Int. Cl.
*A61K 31/343* (2006.01)
*A61K 31/365* (2006.01)
*C07D 307/77* (2006.01)
*C07D 407/02* (2006.01)
*C07D 493/08* (2006.01)

(52) U.S. Cl. ...................... 514/463; 514/468; 549/296; 549/298

(58) Field of Classification Search ................ 549/298, 549/297, 296; 514/463, 468
See application file for complete search history.

(56) References Cited

OTHER PUBLICATIONS

Alexandre, F.-R., et al., "A New Synthetic Route to β-Unsubstituted β-Lactones by Intramolecular Cyclization," *Tetrahedron* 2000, 56: 3921-3926 (Exhibit 1).
Backman, C., et al., "Systemic Administration of a Nerve Growth Factor Conjugate Reverses Age-Related Cognitive Dysfunction and Prevents Cholinergic Neuron Atrophy," *J. Neurosci.* 1996, 16: 5437-5442 (Exhibit 2).
Corey, E. J., et al., "Stereospecific Total Synthesis of Gibberellic Acid. A Key Tricyclic Intermediate," *J. Am. Chem. Soc.* 1978, 100: 8031-8034 (Exhibit 3).
Dauben, W. G., et al., "Simple, Efficient Total Synthesis of Cantharidin via a High-Pressure Diels-Alder Reaction," *J. Am. Chem. Soc.* 1980, 102: 6893-6894 (Exhibit 4).
Defoin, A., et al., "158. From 1-(Silyloxy)butadiene to 4Amino-4-deoxy-DL-erythrose and to 1-Amino-1-deoxy-DL-erythriol Derivatives via hetero-Diels-Alder Reactions with Acylnitroso Dienophiles," *Helv. Chim. Acta* 1991, 74: 1653-1670 (Exhibit 5).

Gash, D. M., et al., "Functional recovery in parkinsonian monkeys treated with GDNF." *Nature* 1996, 380: 252-255 (Exhibit 6).
Hefti, F., "Pharmacology of Neurotrophic Factors," *Annu. Rev. Pharmacol. Toxicol.* 1997, 37: 239-67 (Exhibit 7).
Henbest, H. B. and Wilson, R. A. L., "Stereospecific Cis-Epoxidation of Cyclic Allylic Alcohols," *Chemistry and Industry (London)* 1956, 659 (Exhibit 8).
Huang, J.-M., et al., "Structures of merrilactones B and C, novel anislactone-type sesquiterpenes from *Illicium merrillianum*, and chemical conversion of anislactone B to merrilactone A," *Tetrahedron* 2001, 57: 4691-4698 (Exhibit 9).
Huang, J.-M., et al., "Merrilactone A, a novel neurotrophic sesquiterpene dilactone from *Illicium merrillianum*," *Tet. Lett.* 2000, 41: 6111-6114 (Exhibit 10).
Jaeschke, G. and Seebach, D., "Highly Enantioselective Ring Opening of Cyclic Meso-Anhydrides to Isopropyl Hemiesters with Ti-TADDOLates: An Alternative to Hydrolytic Enzymes?," *J. Org. Chem.* 1998, 63: 1190-1197 (Exhibit 11).
Jasperse, C. P., et al., "Radical Reactions in Natural Product Synthesis," *Chem. Rev.* 1991, 91: 1237-1286 (Exhibit 12).
Johnson, W. S., et al., "A Simple Stereoselective Version of the Claisen Rearrangement Leading to trans-Trisubstituted Olefinic Bonds. Synthesis of Squalene," *J. Am. Chem. Soc.* 1970, 92: 741-743 (Exhibit 13).
Keck, G. E. and Yates, J. B. "Carbon-Carbon Bond Formation via the Reaction of Trialkylallylstannanes with Organic Halides," *J. Am. Chem. Soc.* 1982, 104: 5829-5831 (Exhibit 14).
Marinovic, N. N. and Ramanathan, H. "The Synthesis of Fused and Bridged Ring Systems by Free Radical Carbocyclization. A General Route to Masked 1,4-Diketones," *Tet. Lett.* 1983, 24: 1871-1874 (Exhibit 15).
Pangborn, A.B., et al., "Safe and Convenient Procedure for Solvent Purification," *Organometallics* 1996, 15: 1518-1520 (Exhibit 16).
Rae, I. D. and Serelis, A. K. "Dimethyl cis- and trans-1,2-Dimethyl-cyclohexane-1,2-dicarboxylate," *Aust. J. Chem.* 1990, 43: 1941-1948 (Exhibit 17).
Raucher, S. "The Synthesis of Vinyl Bromides and Allyl Bromides From Monosubstituted Alkenes," *Tet. Lett.* 1977, 44: 3909-3912 (Exhibit 18).
Siegel, G. J. and Chauhan, N. B. "Neurotrophic factors in Alzheimer's and Parkinson's disease brain," *Brain Research Reviews* 2000, 33: 199-227 (Exhibit 19).
Soai, K., et al., "Reduction of Symmetric and Mixed Anhydrides of Carboxylic Acids by Sodium Borohydride with Dropwise Addition of Methanol," *Synthesis* 1987, 647-648 (Exhibit 20).

(Continued)

*Primary Examiner*—Taofiq Solola
(74) *Attorney, Agent, or Firm*—John P. White, Esq.; Cooper & Dunham LLP

(57) ABSTRACT

This invention provides a total synthesis of Merrillactone and Merrilactone analogues for use as neurotrophic agents in the treatment of neurodegenerative diseases. The invention also provides intermediates for use in the synthesis of Merrilactone and its analogues.

9 Claims, No Drawings

OTHER PUBLICATIONS

Ward, D. E. and Rhee, C. K. "Chemoselective reductions with sodium borohydride," *Can. J. Chem.* 1989, 67: 1206-1211 (Exhibit 21).

Ziegler, F. "Stereo- and Regiochemistry of the Claisen Rearrangement: Applications to Natural Products Synthesis," *Acc. Chem. Res.* 1977, 10: 227-232 (Exhibit 22).

Ziegler, V. K., et al., "Synthetiache Versuche in der Gruppe des Cantharidins," *Liebigs Ann.* 1950, 367: 204-214 (Exhibit 23).

TOTAL SYNTHESIS OF MERRILACTONE A

This application claims the benefit of U.S. Provisional Application No. 60/340,449, filed Dec. 14, 2001, the contents of which are hereby incorporated by reference.

This invention has been made with government support under National Institutes of Health grant HL-25848. Accordingly, the U.S. Government has certain rights in the invention.

Throughout this application, various publications are referenced by Roman numeral superscripts. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

Neurotrophic factors are functionally defined as molecules which promote the maintenance and growth of neurons in vitro and in vivo.[1] Among such factors are the nerve growth factor (NGF) and glial cell-derived neurotrophic factor (GDNF). Intraventricular administration of NGF to rats and primates reduces cholinergic neuronal degeneration, with potential implications for the treatment of Alzheimer's disease.[2a,3] GDNF may have consequences in the treatment of Parkinson's disease.[2b] However, optimism along these lines is tempered by concerns as to the pharmacokinetics and bioavailability of polypeptidal factors.[3] It is in this connection that the discovery of non-peptidal small molecules with neurotrophic properties is potentially of great significance.[4] It seems appropriate to explore non-peptidal neurotrophic agents in detail as to their biological function and their usefulness, if any, in the treatment of neurodegenerative diseases. A mastery of the total synthesis of such small-molecule natural products could be most helpful, not only in improving access to these difficultly available agents, but in providing the basis for probing their SAR profiles.

Described below is the total synthesis of the pentacyclic sesquiterpene dilactone, merrilactone A (1). This compound had previously been obtained in 0.004% yield from the methanol extract of the pericarps of *Illicium merrillianum*.[5] Preliminary studies indicated that 1 greatly promotes neurite outgrowth in fetal rat cortical neurons at concentrations as low as 0.1–10 μmol. Further investigations to date have been hampered by the scarcity of the natural merrilactone A.

SUMMARY OF THE INVENTION

This invention provides a total synthesis of Merrillactone and Merrilactone analogues having the structure

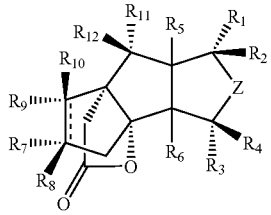

wherein Z is O or >N—X, where X is H, straight or branched substituted or unsubstituted alkyl, alkenyl or alkynyl, or acyl, carbamoyl, cycloalkyl, aryl, heterocycloalkyl, heteroaryl, aralkyl, amino, alkyl amino, or dialkyl amino;

wherein each of $R_1$ and $R_2$ is H or $R_1$ and $R_2$ together are =O;

wherein each of $R_3$ and $R_4$ is H or $R_3$ and $R_4$ together are =O;

wherein each of $R_5$ and $R_6$ is, independently, H, alkyl, aralkyl, or aryl;

wherein each of $R_7$ and $R_8$ is, independently, H or $OR_{14}$, where $R_{14}$ is alkyl or —C(O)—$R_{15}$, where $R_{15}$ is H, —$CH_2R_{16}$, —$CHR_{16}R_{16}$, —$CR_{16}R_{17}R_{16}$, —$OR_{16}$, alkenyl or alkynyl, cycloalkyl, aryl, heterocycloalkyl, heteroaryl, aralkyl, amino, alkyl amino, or dialkyl amino, wherein each $R_{16}$ is straight or branched, substituted or unsubstituted alkyl, alkenyl or alkynyl, cycloalkyl, aryl, heterocycloalkyl, heteroaryl, aralkyl, or amino; and wherein $R_{17}$ is straight or branched, unsubstituted alkyl, alkenyl or alkynyl, cycloalkyl, aryl, heterocycloalkyl, heteroaryl, aralkyl, or amino, or wherein $R_7$ and $R_9$ together are >O;

wherein each of $R_9$ and $R_{10}$ is, independently, H, alkyl, OH, or $OR_{13}$, where $R_{13}$ is an alkyl, an acyl, or an amide, or $R_9$ and $R_{10}$ together are =$CH_2$, or wherein $R_8$ and $R_{10}$ together are >O;

wherein if one of $R_7$ or $R_8$ and one of $R_9$ or $R_{10}$ is absent, a double bond is formed as indicated by the broken line; and wherein each of $R_{11}$ and $R_{12}$ is, independently, H, OH, or $OR_{13}$, where $R_{13}$ is an alkyl, an acyl, or an amide, or $R_{11}$ and $R_{12}$ together are =O, or wherein $R_{12}$ and $R_{10}$ together are >O.

The invention also provides intermediates for use in the synthesis.

The total synthesis of the title compound has been accomplished in 20 steps. The key step is a free radical cyclization of vinyl bromide 29 to afford 30. The synthesis also features an efficient Diels-Alder reaction of 2,3-dimethylmaleic anhydride with 1-(tert-butyldimethylsiloxy)-butadiene. The oxetane moiety of merrilactone A is fashioned via a Payne-like rearrangement of a hydroxyepoxide (see 2->1).

DETAILED DESCRIPTION OF THE INVENTION

In one embodiment, this invention provides a compound having the structure

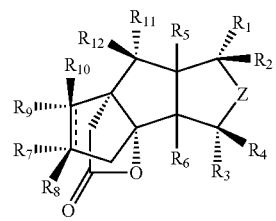

wherein Z is O or >N—X, where X is H, straight or branched substituted or unsubstituted alkyl, alkenyl or alkynyl, or acyl, carbamoyl, cycloalkyl, aryl, heterocycloalkyl, heteroaryl, aralkyl, amino, alkyl amino, or dialkyl amino;

wherein each of $R_1$ and $R_2$ is H or $R_1$ and $R_2$ together are =O;

wherein each of $R_3$ and $R_4$ is H or $R_3$ and $R_4$ together are =O;

wherein each of $R_5$ and $R_6$ is, independently, H, alkyl, aralkyl, or aryl;

wherein each of $R_7$ and $R_8$ is, independently, H or $OR_{14}$,
 where $R_{14}$ is alkyl or —C(O)—$R_{15}$,
  where $R_{15}$ is H, —$CH_2R_{16}$, —$CHR_{16}R_{16}$, —$CR_{16}R_{17}R_{16}$, —$OR_{16}$, alkenyl or alkynyl, cycloalkyl, aryl, heterocycloalkyl, heteroaryl, aralkyl, amino, alkyl amino, or dialkyl amino,
   wherein each $R_{16}$ is straight or branched, substituted or unsubstituted alkyl, alkenyl or alkynyl, cycloalkyl, aryl, heterocycloalkyl, heteroaryl, aralkyl, or amino; and
   wherein $R_{17}$ is straight or branched, unsubstituted alkyl, alkenyl or alkynyl, cycloalkyl, aryl, heterocycloalkyl, heteroaryl, aralkyl, or amino,
  or wherein $R_7$ and $R_9$ together are >O;

wherein each of $R_9$ and $R_{10}$ is, independently, H, alkyl, OH, or $OR_{13}$, where $R_{13}$ is an alkyl, an acyl, or an amide, or $R_9$ and $R_{10}$ together are =$CH_2$,
 or wherein $R_8$ and $R_{10}$ together are >O;

wherein if one of $R_7$ or $R_8$ and one of $R_9$ or $R_{10}$ is absent, a double bond is formed as indicated by the broken line; and wherein each of $R_{11}$ and $R_{12}$ is, independently, H, OH, or $OR_{13}$, where $R_{13}$ is an alkyl, an acyl, or an amide, or $R_{11}$ and $R_{12}$ together are =O,
 or wherein $R_{12}$ and $R_{10}$ together are >O.

In another embodiment of the compound Z is >N—X, where X is H, straight or branched substituted or unsubstituted alkyl, alkenyl or alkynyl, or acyl, carbamoyl, cycloalkyl, aryl, heterocycloalkyl, heteroaryl, aralkyl, amino, alkyl amino, or dialkyl amino.

In yet another embodiment of the compound Z is O or >N—X, where X is H, straight or branched alkyl, alkenyl or alkynyl, or acyl, carbamoyl, cycloalkyl, aryl, heterocycloalkyl, heteroaryl, aralkyl, amino, alkyl amino, or dialkyl amino;

wherein each of $R_1$ and $R_2$ is H or $R_1$ and $R_2$ together are =O;

wherein each of $R_3$ and $R_4$ is H or $R_3$ and $R_4$ together are =O;

wherein each of $R_5$ and $R_6$ is, independently, H, alkyl, or aralkyl;

wherein each of $R_7$ and $R_8$ is, independently, H or $OR_{14}$,
 where $R_{14}$ is alkyl or —C(O)—$R_{15}$,
  where $R_{15}$ is H, —$CH_2R_{16}$, —$CHR_{16}R_{16}$, —$CR_{16}R_{17}R_{16}$, —$OR_{16}$, cycloalkyl, aryl, or aralkyl,
   wherein each $R_{16}$ is alkyl, cycloalkyl, or aryl, aralkyl; and
   wherein $R_{17}$ is alkyl, cycloalkyl, aryl, or aralkyl,
  or wherein $R_7$ and $R_9$ together are >O;

wherein each of $R_9$ and $R_{10}$ is, independently, H, alkyl, OH, or $OR_{13}$, where $R_{13}$ is an alkyl, an acyl, or an amide, or $R_9$ and $R_{10}$ together are =$CH_2$,
 or wherein $R_8$ and $R_{10}$ together are >O;

wherein if one of $R_7$ or $R_8$ and one of $R_9$ or $R_{10}$ is absent, a double bond is formed as indicated by the broken line; and wherein each of $R_{11}$ and $R_{12}$ is, independently, H, OH, or $OR_{13}$, where $R_{13}$ is an alkyl, an acyl, or an amide, or $R_{11}$ and $R_{12}$ together are =O,
 or wherein $R_{12}$ and $R_{10}$ together are >O.

In another embodiment, the compound hasing the structure

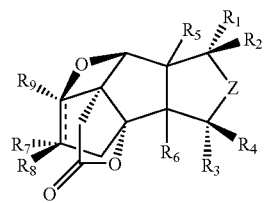

wherein Z is >O;

wherein each of $R_1$ and $R_2$ is H, or $R_1$ and $R_2$ together are =O;

wherein each of $R_3$ and $R_4$ is H, or $R_3$ and $R_4$ together are =O;

wherein each of $R_5$ and $R_6$ is, independently, H, alkyl, aralkyl, or aryl;

wherein each of $R_7$ and $R_8$ is, independently, H or $OR_{14}$,
 where $R_{14}$ is alkyl or —C(O)—$R_{15}$,
  where $R_{15}$ is H, —$CH_2R_{16}$, —$CHR_{16}R_{16}$, —$CR_{16}R_{17}R_{16}$, —$OR_{16}$, alkenyl or alkynyl, cycloalkyl, aryl, heterocycloalkyl, heteroaryl, aralkyl, amino, alkyl amino, or dialkyl amino,
   wherein each $R_{16}$ is straight or branched, substituted or unsubstituted alkyl, alkenyl or alkynyl, cycloalkyl, aryl, heterocycloalkyl, heteroaryl, aralkyl, or amino; and
   wherein $R_{17}$ is straight or branched, unsubstituted alkyl, alkenyl or alkynyl, cycloalkyl, aryl, heterocycloalkyl, heteroaryl, aralkyl, or amino; and wherein $R_9$ is H, alkyl, OH, or $OR_{13}$, where $R_{13}$ is an alkyl, an acyl, or an amide.

In this embodiment, $R_9$ may be H, alkyl or $OR_{13}$, where $R_{13}$ is an alkyl, an acyl, or an amide.

Also disclosed is a compound wherein $R_1$ and $R_2$ together are =O;

wherein each of $R_3$ and $R_4$ is H;

wherein each of $R_5$ and $R_6$ is, independently, H, alkyl, or aralkyl;

wherein each of $R_7$ and $R_8$ is, independently, H or $OR_{14}$,
 where $R_{14}$ is alkyl or —C(O)—$R_{15}$,
  where $R_{15}$ is H, —$CH_2R_{16}$, —$CHR_{16}R_{16}$, —$CR_{16}R_{17}R_{16}$, —$OR_{16}$, alkenyl or alkynyl, cycloalkyl, aryl, heterocycloalkyl, heteroaryl, aralkyl, amino, alkyl amino, or dialkyl amino,
   wherein each $R_{16}$ is straight or branched, substituted or unsubstituted alkyl, alkenyl or alkynyl, cycloalkyl, aryl, heterocycloalkyl, heteroaryl, aralkyl, or amino; and
   wherein $R_{17}$ is straight or branched, unsubstituted alkyl, alkenyl or alkynyl, cycloalkyl, aryl, heterocycloalkyl, heteroaryl, aralkyl, or amino; and wherein $R_9$ is alkyl.

In yet another embodiment, the invention provides a compound having the structure

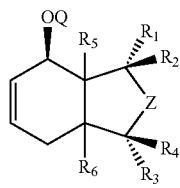

wherein Z is O or >N—X, where X is H, straight or branched substituted or unsubstituted alkyl, alkenyl or alkynyl, or acyl, carbamoyl, cycloalkyl, aryl, heterocycloalkyl, heteroaryl, aralkyl, amino, alkyl amino, or dialkyl amino;

wherein each of $R_1$ and $R_2$ is H or $R_1$ and $R_2$ together are =O;

wherein each of $R_3$ and $R_4$ is H or $R_3$ and $R_4$ together are =O;

wherein each of $R_5$ and $R_6$ is, independently, alkyl, aralkyl, or aryl; and where Q is H or a silyl protecting group.

The compound may have the structure

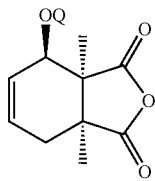

The compound may also have the structure

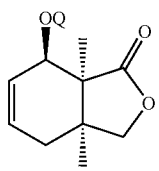

The compound may further have the structure

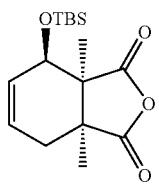

The compound also may have the structure

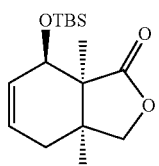

In a further embodiment, this invention provides a compound having the structure

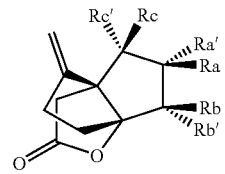

wherein each of Ra, Ra', Rb, and Rb' is independently H, alkyl, alkenyl, alkynyl, acyl, or carbamoyl, or either Ra and Rb or Ra' and Rb' together with the carbons to which they are attached form a substituted or unsubstituted five or six member ring; and wherein each of Rc and Rc' is, independently, H, OH or OR, wherein R is alkyl, acyl or Q, where Q is a silyl protecting group, or both Rc and Rc' together are =O.

This invention also provides a process for forming a cyclic ring in the compound so as to produce the compound having the structure

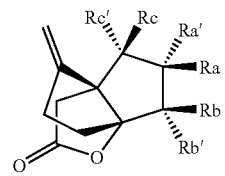

wherein each of Ra, Ra', Rb, and Rb' is independently H, alkyl, alkenyl, alkynyl, acyl, or carbamoyl, or either Ra and Rb or Ra' and Rb' together with the carbons to which they are attached form a substituted or unsubstituted five or six member ring; and wherein each of Rc and Rc' is, independently, H, OH or OR, wherein R is alkyl, acyl or Q, where Q is a silyl protecting group, or both Rc and Rc' together are =O, comprising treating a compound having the structure

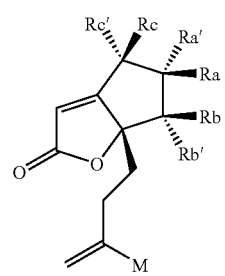

where M is Br or I, with $Bu_3SnH$ or tris-(trimethyl silyl)-silane ($(TMS)_3SiH$) and a free radical initiator so as to thereby produce the compound.

The process can produce a compound having the structure

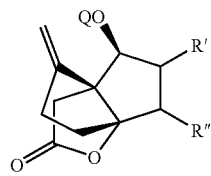

where Q is a silyl protecting group; and
where each of R' and R" is independently alkyl, alkenyl, alkynyl, acyl, or carbamoyl, or R' and R" together form a substituted or unsubstituted five or six member ring, by treating a compound having the structure

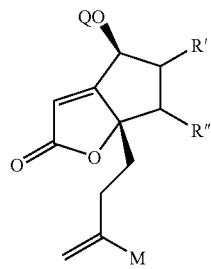

where M is Br or I,
with Bu₃SnH or tris-(trimethyl silyl)-silane ((TMS)₃SiH) and a free radical initiator so as to thereby produce the compound.

The process may also produce a compound having the structure

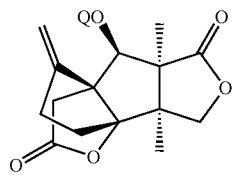

by treating a compound having the structure

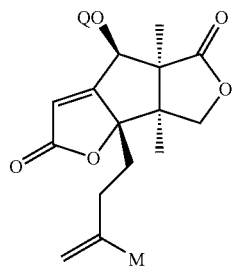

where Q is a silyl protecting group; and
where M is Br or I, with Bu₃SnH or tris-(trimethyl silyl)-silane ((TMS)₃SiH) and a free radical initiator so as to thereby produce the compound.

Furthermore, the process can produce a compound having the structure

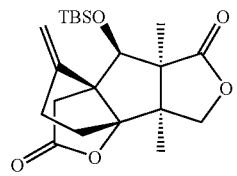

by treating a compound having the structure

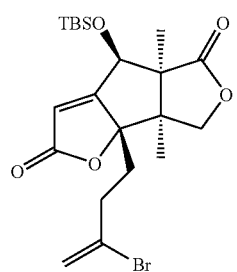

with Bu₃SnH and AIBN so as to thereby produce the compound.

This invention also provides a process for synthesizing a compound having the structure

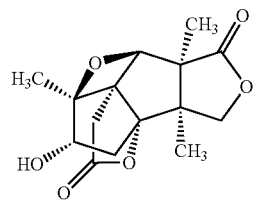

comprising
a) reacting a compound having the structure

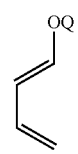

where Q is a silyl protecting group, with a compound having the structure

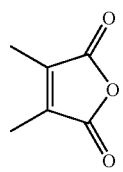

at a temperature of from about 140° C. to 230° C. to produce a compound having the structure

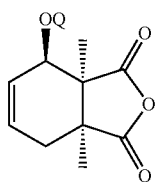

b) reacting the compound of step a) with MeONa to produce

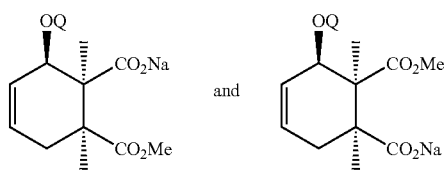

c) treating both products of step b) with ClCO₂Me to produce

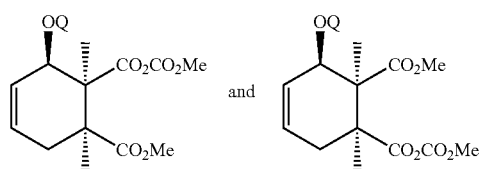

d) treating both products, of step c) with NaBH₄ to produce

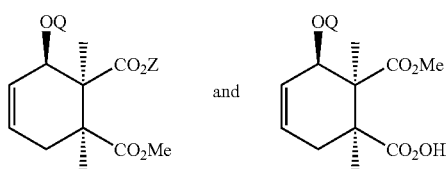

Z = CO₂Me; or Z = H e) treating the products of step d) with LiOH to produce

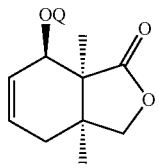

f) treating the product of step e) with O₃ followed by Bn₂NH*TFA to produce

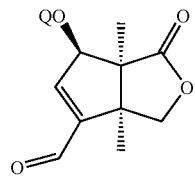

g) treating the product of step f) with NaBH₄ to produce

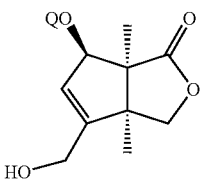

h) treating the product of step g) with MeC(OEt)₃ to produce

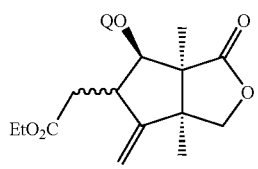

i) treating the product of step h) LiOH and I₂ and to produce

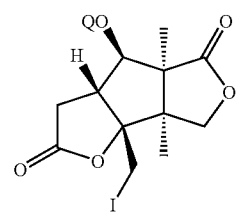

j) treating the product of step i) with allylSnBu₃ to produce

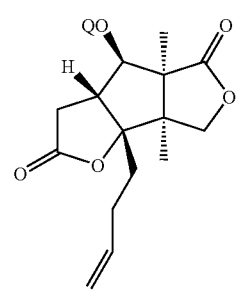

k) treating the product of step j) with LHMDS, TMSCl and PhSeCl, and then with PhSeBr and MeCN to produce

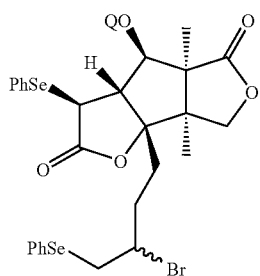

l) treating the product of step k) with O₃, CH₂Cl₂ and 1-hexene to produce

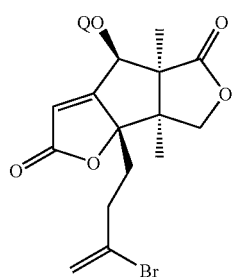

m) treating the product of step l) with Bu₃SnH and AIBN to produce

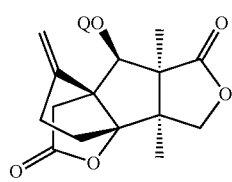

n) treating the product of step m) with TsOH to produce

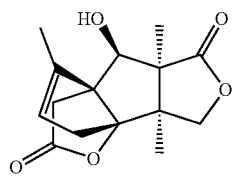

o) treating the product of step n) with mCPBA or a dimethyldioxirane to produce

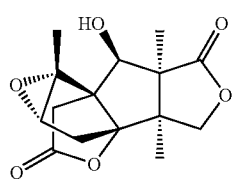

p) treating the product of step o) with an acid to produce the compound.

The process can also synthesize a compound having the structure

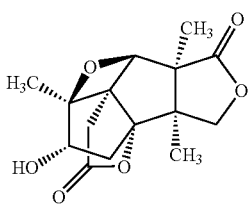

comprising a) reacting a compound having the structure

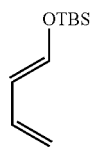

with a compound having the structure

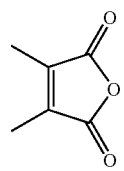

at a temperature of from about 160° C. to 180° C. to produce a compound having the structure

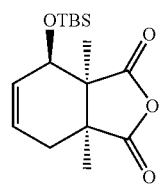

b) reacting the compound of step a) with MeONa and MeOH to produce

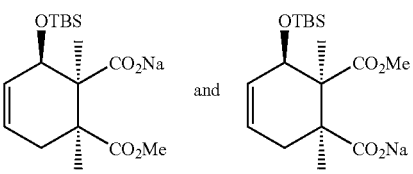

c) treating both products of step b) with ClCO₂Me in THF to produce

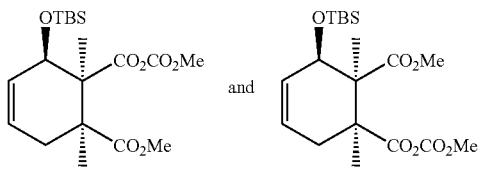

d) treating both products of step c) with NaBH$_4$ and MeOH to produce

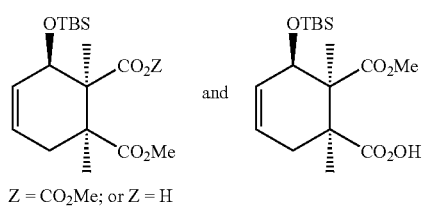

Z = CO$_2$Me; or Z = H e) treating the products of step d) with aqueous LiOH to produce

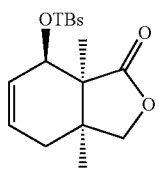

f) treating the product of step e) first with O$_3$ and PPh$_3$, and then with Bn$_2$NH*TFA in benzene to produce

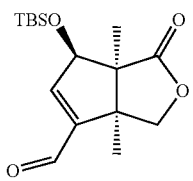

g) treating the product of step f) with NaBH$_4$ and CH$_2$Cl$_2$ in MeOH to produce

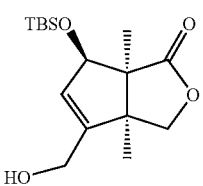

h) treating the product of step g) with MeC(OEt)$_3$ and PivOH to produce

i) treating the product of step h) first with aqueous LiOH and MeOH, and then with I$_2$ and NaHCO$_3$ in THF to produce

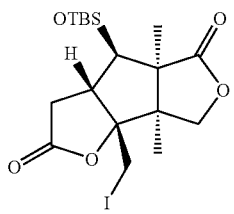

j) treating the product of step i) with allylSnBu$_3$, AIBN and PhH to produce

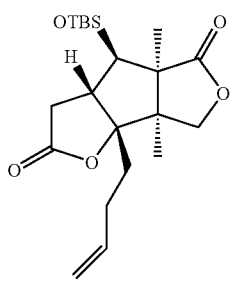

k) treating the product of step j) first with LHMDS, TMSCl and PhSeCl, and then with PhSeBr and MeCN to produce

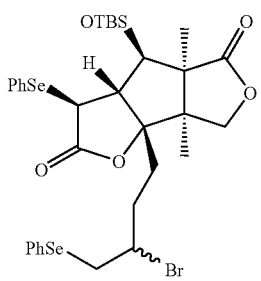

l) treating the product of step k) first with O$_3$, CH$_2$Cl$_2$ and 1-hexene, and then with PhH, NEt$_3$ under reflux conditions to produce

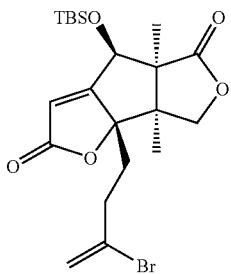

m) treating the product of step l) with Bu₃SnH and AIBN, and PhH to produce

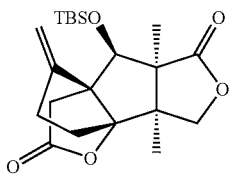

n) treating the product of step m) with aqueous TsOH and PhH under reflux conditions to produce

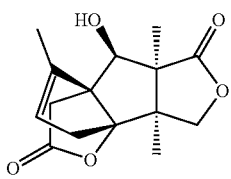

o) treating the product of step n) with mCPBA and CH₂Cl₂ to produce

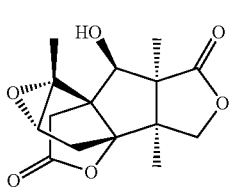

p) treating the product of step o) with aqueous TsOH and CH₂Cl₂ to produce the compound.

The abbreviations used are defined below:
TFA=trifluoroacetic acid
THF=tetrahydrofuran
Bn₂NH.TFA=dibenzylammonium trifluoroacetate
LHMDS=lithium hexamethyldisilazide
TBS=tert-butyldimethylsilyl
PivOH=pivalic acid
AIBN=azobis-(isobutyronitrile)
PhH=benzene
MeCN=acetonitrile
MeOH=methanol
mCPBA=meta-chloroperbenzoic acid
TsOH=para-toluenesulfonic acid The invention further contemplates the use of prodrugs which are converted in vivo to the therapeutic compounds of the invention (see, e.g., R. B. Silverman, 1992, "The Organic Chemistry of Drug Design and Drug Action", Academic Press, Chapter 8, the entire contents of which are hereby incorporated by reference). Such prodrugs can be used to alter the biodistribution (e.g., to allow compounds which would not typically enter the reactive site of the protease) or the pharmacokinetics of the therapeutic compound.

Certain embodiments of the disclosed compounds can contain a basic functional group, such as amino or alkylamino, and are thus capable of forming pharmaceutically acceptable salts with pharmaceutically acceptable acids, or contain an acidic functional group and are thus capable of forming pharmaceutically acceptable salts with bases. The term "pharmaceutically acceptable salts" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

It will be noted that the structure of some of the compounds of this invention includes asymmetric carbon atoms and thus occur as racemates and racemic mixtures, single enantiomers, diastereomeric mixtures and individual diastereomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and/or by stereochemically controlled synthesis.

Compounds discussed above, such a merrilactone A, promote the maintenance and growth of neurons both in vivo and in vitro and promote neurite outgrowth in fetal rat cortical neurons. Based on their chemical and structural similarities to merrilactone A, such activity of the disclosed compounds is not expected. Furthermore, the activity of the disclosed compounds both in vivo and in vitro can be determined by using published test procedures.

EXAMPLES AND DISCUSSION

Example 1

The challenge of creating the densely oxygenated, highly compact architecture of merrilactone A in the laboratory added to the attractiveness of the project. One of the provocative features of the target system is the presence of an oxetane linkage bridging the β-faces of C7 and C1. We envisioned the possibility that such an oxetane might arise by Payne-like rearrangement of α-epoxide 2. It was further conjectured that isomerization of exo-olefin 3 followed by epoxidation would lead to 2. A critical step en route to 3 might be a free radical cyclization[6] of a substrate of type 4, enabling formation of a new quaternary center in a densely substituted environment. It was further anticipated that suitable two-fold oxidation of 5 might provide the required complementary functionality of 4. This line of reasoning invited a proposal that overall "allyl-lactonization" could be used to convert 6 to 5. Recognition of the γ,δ-unsaturated acid character of 6 called to mind the possibility of reaching this intermediate by Claisen rearrangement via 7. Preparation of 7 was to be achieved through a ring cleavage-reclosure sequence from 8. The latter structure, in turn, was suggestive of a Diels-Alder based construction. However, the prospects of a direct cycloaddition between 9 and 10 to reach 8 were not promising. Even uncongested butenolides are not particularly powerful dienophiles. The presence of the two methyl groups, creating a tetrasubstituted "dienophilic" double bond, was likely to preclude such a cycloaddition. Hence, we sought to compensate for the expected steric impediment through recourse to a more reactive dienophile substructure (cf. 12). The development of a scheme which, in effect, circumvents the inertness of 10 was a key challenge to our prospectus.

resulting salts (14 and 15) with ClCO$_2$Me in THF afforded mixed anhydrides 16 and 17. Remarkably, exposure of this mixture to the action of NaBH$_4$ and methanol[9] led to clean reduction of 17 while leaving 16 unchanged. (The inertness of the C12 carbonyl in 16 may be due to its axial orientation.) Subsequent addition of lithium hydroxide to the mixture afforded compounds 18 and 20, easily separable by a simple extraction. Treatment of 18 with LiBHEt$_3$[11] also afforded 20. The regioconvergence of this scheme obviated any need for chromatographic separation of intermediates and afforded 20 in 78% overall yield from 13.

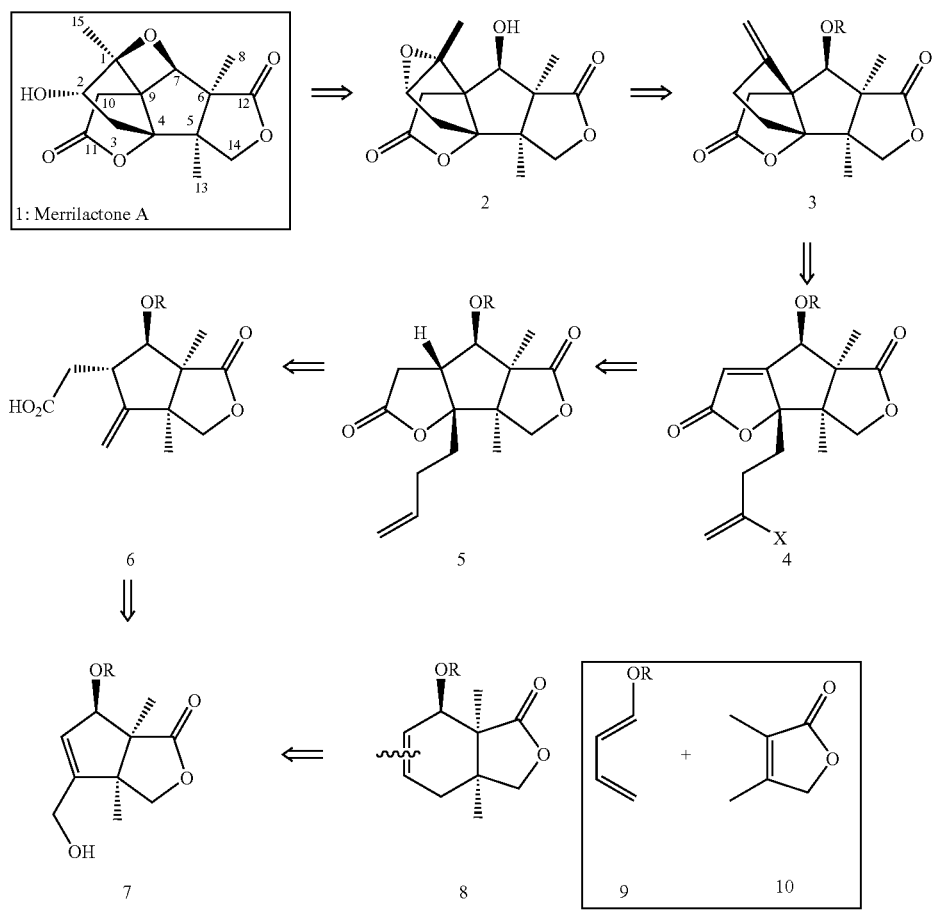

Scheme 1

The reaction of 2,3-dimethylmaleic anhydride (12)[7] and 11[8] occurred under the conditions shown, to afford 13 in 74% yield. We next turned to regioselective reduction of the C14 carbonyl group (future merrilactone A numbering). Attempted reductions with conventional borohydride reagents led to complex mixtures. This lack of selectivity necessitated a somewhat awkward, but high yielding, circumvention. It was established that ring opening of 13 with sodium methoxide proceeded smoothly. Treatment of the Scheme 2

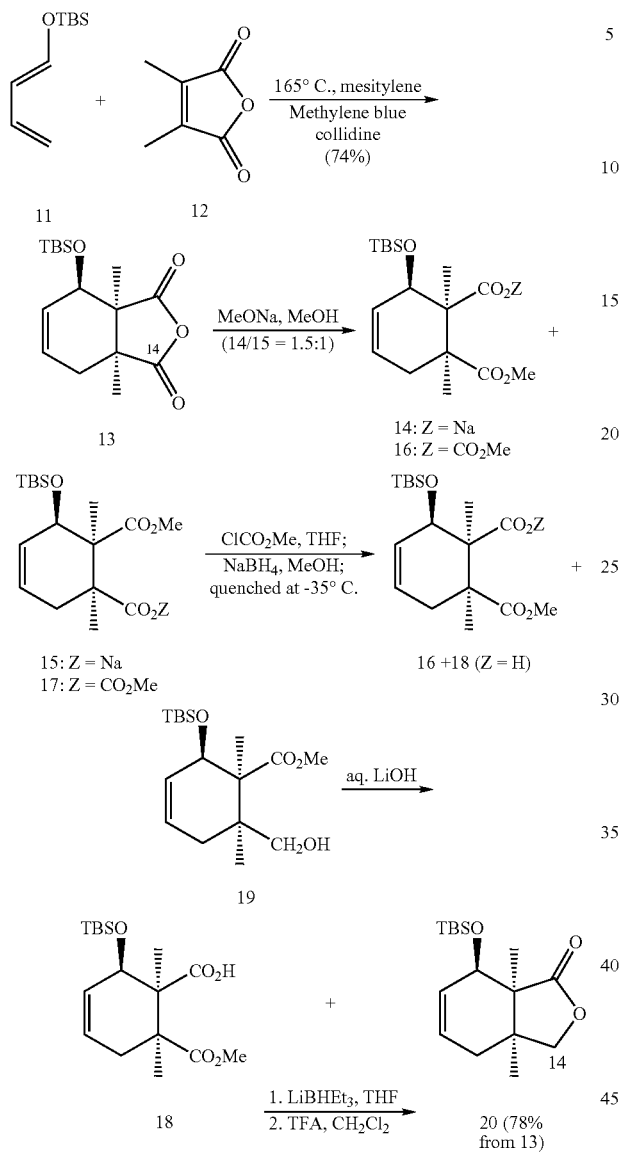

Scheme 3

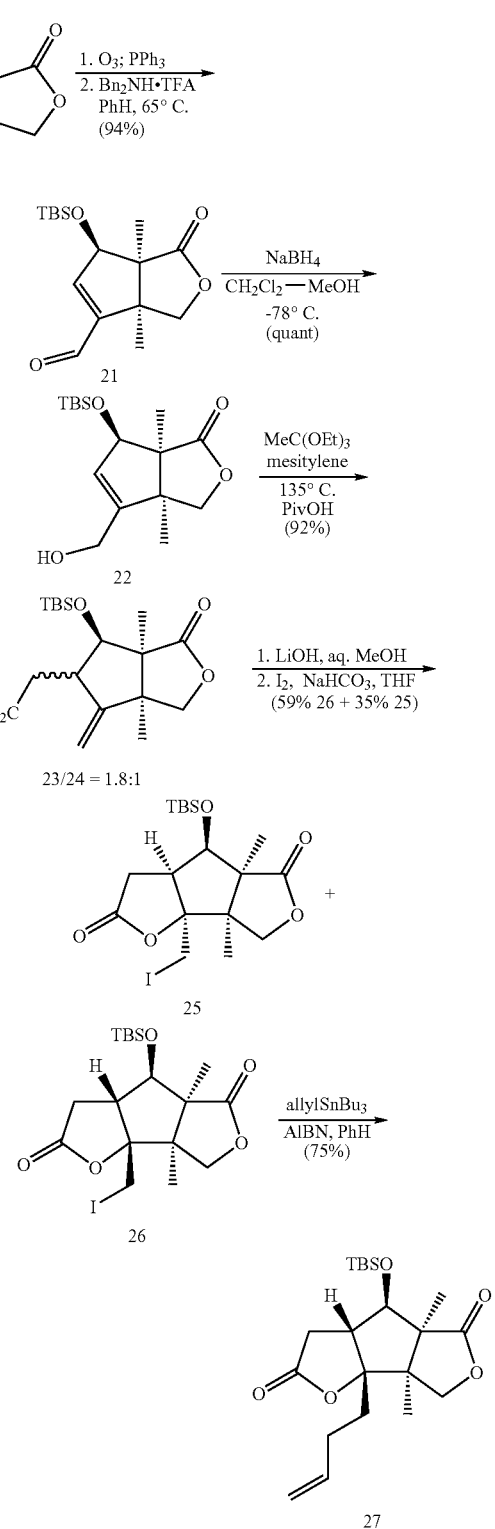

The stage was now set for the ring cleavage-reclosure sequence (cf. 8→7 in retrosynthesis plan). Ozonolysis of 20 followed by reductive workup, as shown, led to a dialdehyde, which on aldol condensation using Corey's conditions[12] afforded the cyclodehydrated product 21 in high yield. Following reduction[13] of the aldehyde function, allylic alcohol 22 was in hand. The next stage called for Claisen rearrangement to reach 23. The most advantageous way to achieve this result proved to be via the Johnson orthoester protocol.[14] The mixture of esters (23/24~1.8:1) thus produced was hydrolyzed, and the resultant acids subjected to iodolactonization. Two crystalline and chromatographically separable iodolactones, 25 and 26, were obtained in 35 and 59% yields, respectively. Chain extension of the required "anti-backbone" isomer 26 was accomplished (75% yield) by the elegant C-allylation method of Keck.[15]

As noted above, (cf. 5→4 in the retrosynthesis) oxidation at two sites would be required to complete the setting for the proposed key cyclization step (cf. 4→3). An efficient sequence to deal with potentially awkward functional group management issues in advancing beyond 27 was developed. Thus, selenenylation at C10 was accomplished via an intermediate silyl ketene acetal. With this subgoal achieved, bromoselenenylation of the terminal vinyl group of 27 was conducted according to methodology introduced some years ago by Rauscher.[16] Concurrent oxidative deselenation afforded the desired 29. The setting for testing the key free radical cyclization was at hand. Our initial concerns that the steric congestion at the $sp^2$ center at C9 might lead to the competitive reduction of the vinylic radical, fortunately, proved groundless. In the event, treatment of 29 under the standard conditions[6a] afforded a 90% yield of 30.

Isomerization of the exo methylene group in 30 envisioned at the planning stage was accomplished concurrently with liberation of the C7 β-alcohol. While hydroxyl groups have often been used to direct epoxidation with peracids in a syn sense,[17] in the case at hand the congested nature of the β-face of the C1–C2 double bond is such that epoxidation occurs primarily (3.5:1) from its α-face (see compound 2).[18] In the final step of the synthesis, merrilactone A is produced by an acid-induced homo-Payne rearrangement (see 2→1). The spectroscopic properties of 31, 2, and 1 were in complete accord with the published data.[5b] Further confirmation came from the identity of the NMR spectra of synthetic (±)-1 with those of natural merrilactone A.

In summary, a total synthesis of merrilactone A has been accomplished. The first generation route described above provides, for the first time, ample material for extensive preclinical evaluations of merrilactone A. The chemistry developed to date (20 steps, 10.7% overall yield) is amenable to scale-up to multigram levels. Moreover, the use of dimethylmaleic anhydride (12) as a dienophile leading to the incorporation of two angular methyl groups has broad potential implications which warrant follow-up.

Scheme 4

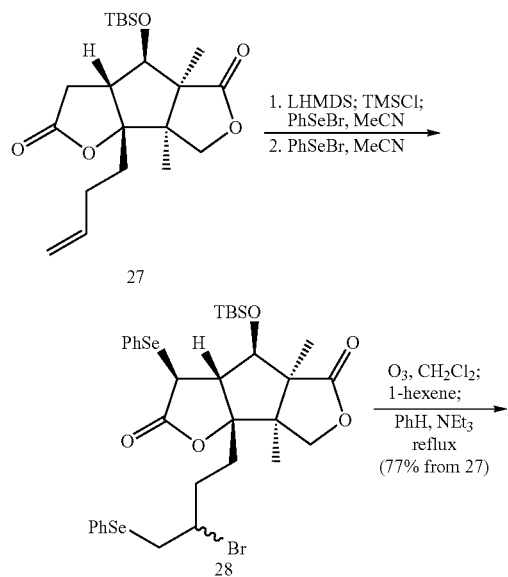

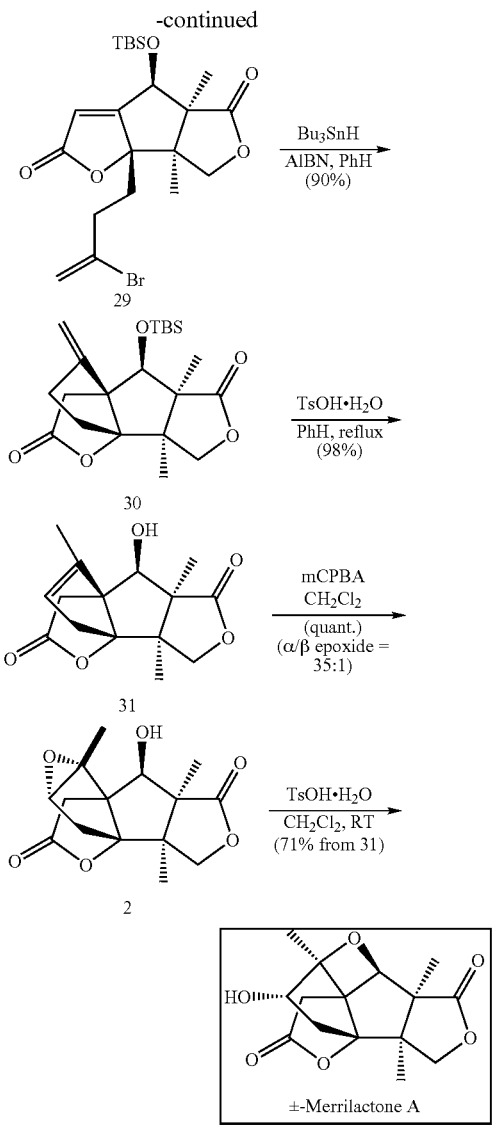

Experimental Details for Example 1

All reactions were carried out under an argon atmosphere. Tetrahydrofuran, diethyl ether, and dichloromethane were purified by passing through solvent columns.[10] Other solvents were obtained commercially and were used as received. 1-(t-butyldimethylsilyloxy)-1,3-butadiene was prepared according to a literature procedure. All other reagents were reagent grade and purified where necessary. Reactions were monitored by thin layer chromatography (TLC) using EM Science 60F silica gel plates. Flash column chromatography was performed over Scientific Adsorbents Inc. silica gel (32–63 μm). Melting points were measured on a Thomas Hoover capillary melting point apparatus and are uncorrected. $^1$H NMR and $^{13}$C NMR spectra were recorded on Bruker-Spectrospin spectrometers. The chemical shifts are reported as δ values (ppm) relative to TMS. Infrared spectra were recorded on a Perkin-Elmer Paragon 1000 FT-IR Spectrophotometer (NaCl plates, film). Low-Resolution mass spectral analyses were performed on a Jeol LC/MS system using chemical ionization.

Diels-Alder Adduct 13. A flask containing a mixture of 2,3-dimethylmaleic anhydride (2.520 g, 20.0 mmol), 1-(t-butyldimethylsilyloxy)-1,3-butadiene (5.53 g, 30.0 mmol), symm-collidine (150 mg), Methylene Blue (5 mg), and mesitylene (6.2 mL) was purged with argon several times and stirred under reflux in an oil bath at 165° C. for 2.5 days. The solvents were removed by Kugelrohr distillation at 100° C., and the residue was purified by flash chromatography (hexanes/EtOAc 19:1) to afford 4.604 g (74% yield) of the product which crystallized upon standing. $^1$H NMR (CDCl$_3$, 400 MHz): δ −0.03 (s, 3H), 0.01 (s, 3H), 0.79 (s, 9H), 1.16 (s, 3H), 1.31 (s, 3H), 2.00 (dd, J=21, J=4, 1H), 2.99 (d, J=21, 1H), 4.13 (d, J=5.7, 1H), 5.96 (m, 2H); $^{13}$C NMR (CDCl$_3$, 100 MHz): −5.6, −4.4, 14.7, 17.7, 25.3, 25.6, 30.0, 44.2, 53.9, 70.2, 126.9, 130.1, 175.4, 176.7; IR (NaCl, cm$^{-1}$): 1784 s, 1852 m (anhydride C=O); MS Found: 311.1 (M+1), Calc. 310.16; Mp 62–63° C.

Lactone 20. Part A. A stirring mixture of Diels-Alder Adduct 13 (1.240 g, 4.00 mmol) and dry methanol (10 mL) was treated at RT with 25% methanolic solution of MeONa (0.92 mL, 4.02 mmol). After 15 minutes, the mixture was rotary evaporated, and the residue was coevaporated twice with benzene to dryness. The resulting viscous oil was dissolved in THF (10 mL), the solution was cooled in an ice bath and treated with ClCO$_2$Me (0.400 mL, 5.18 mmol). After 20 minutes, the mixture was cooled to −78° C., and solid NaBH$_4$ (400 mg, 10.57 mmol) was added, followed by dropwise addition of dry MeOH (1.60 mL). The mixture was allowed to warm up to −35° C., quenched with saturated aqueous ammonium chloride (6 mL), warmed to RT, diluted with water, and extracted twice with Et$_2$O. The aqueous phase was acidified to pH 3–4 with 1 M HCl and extracted twice with Et$_2$O. The combined ethereal extract was evaporated, the residue dissolved in THF (12 mL), and stirred vigorously with aqueous LiOH (4 mL, 5%) for 1.5 hours. The mixture was diluted with water and extracted 3 times with hexanes. The hexane extract (containing almost pure lactone 20) was washed twice with 1 M NaOH, then brine, dried with Na$_2$SO$_4$, and set aside.

Part B. The combined alkaline aqueous phase from the previous step was acidified with 1 M HCl and extracted 3 times with Et$_2$O. The ethereal solution was dried over MgSO$_4$, rotary evaporated, and the residue was coevaporated with benzene. The resulting crude half-ester 18 (758 mg, 2.21 mmol) was cooled in an ice bath and treated with LiBHEt$_3$ (1M in THF, 12 mL). After stirring overnight at RT, the mixture was cooled again in an ice bath, quenched with 1 M NaOH (8 mL), and then carefully treated with 10% H$_2$O$_2$ (18 mL) added in several portions to avoid excessive heating. After stirring for 0.5 hour, the solution was acidified with 1 M HCl to pH 5–6 and extracted with Et$_2$O twice. The viscous residue on the bottom of the flask was shaken vigorously with 1 M HCl and Et$_2$O until completely dissolved. The resulting two-phase mixture was combined with the aqueous phase, acidified to pH 5–6 again, and extracted with ether twice. The combined ethereal extract was washed with brine once, dried over MgSO$_4$, rotary evaporated, redissolved in 10 mL of CH$_2$Cl$_2$, and treated with TFA (0.04 mL). After 3 days, this mixture was combined with the previously obtained hexane solution of lactone 20, evaporated, and subjected to flash chromatography (hexanes/EtOAc 19:1) to afford 925 mg (78% yield) of the product as colorless oil which crystallized upon standing. $^1$H NMR (CDCl$_3$, 500 MHz): δ 0.05 (s, 3H), 0.08 (s, 3H), 0.86 (s, 9H), 1.06 (s, 3H), 1.09 (s, 3H), 2.00 (ddd, J=19.3, J=1.9, J=1.0, 1H), 2.14 (ddd, J=19.3, J=2.1, J=1.6, 1H), 3.73 (d, J=7.6, 1H), 3.97 (d, J=4.7, 1H), 4.32 (d, J=7.6, 1H), 5.76–5.83 (m, 2H); $^{13}$C NMR (CDCl$_3$, 100 MHz): −5.4, −4.1, 16.2, 17.7, 25.6, 26.2, 30.7, 39.2, 50.1, 70.0, 75.4, 126.4, 126.7, 179.6; IR (NaCl, cm$^{-1}$): 1777s (C=O); MS Found: 297.1 (M+1), Calc. 296.18; Mp 44–44.5° C.

Unsaturated aldehyde 21. A solution of lactone 20 (592 mg, 2 mmol) in a mixture of dry CH$_2$Cl$_2$ (20 mL) and dry MeOH (20 mL) was ozonated at −78° C. until blue color appeared, then purged with oxygen until colorless, treated with PPh$_3$ (630 mg, 2.4 mmol, added in 6 mL of CH$_2$Cl$_2$), and allowed to warm up to RT. The solvents were removed by rotary evaporation, the residue was coevaporated with benzene and dissolved in benzene (40 mL). Dibenzylammonium trifluoroacetate (124 mg, 0.4 mmol) was added, and the resulting solution was stirred at 63° C. for 9 hours. The solvent was evaporated, and the residue was chromatographed (hexanes/ethyl acetate 9:1) to afford 580 mg (94% yield) of the product as colorless oil which crystallized upon standing. $^1$H NMR (CDCl$_3$, 400 MHz): δ 0.12 (s, 3H), 0.15 (s, 3H), 0.90 (s, 9H), 1.25 (s, 3H), 1.33 (s, 3H), 4.04 (d, J=9.2, 1H), 4.26 (d, J=9.2, 1H), 4.61 (d, J=2.2, 1H), 6.62 (d, J=2.2, 1H), 9.82 (s, 1H); $^{13}$C NMR (CDCl$_3$, 100 MHz): −5.1, −4.7, 16.3, 17.5, 18.0, 25.6, 53.2, 57.4, 75.8, 82.9, 132.9, 149.3, 149.6, 176.1, 189.8; IR (NaCl, cm$^{-1}$): 1688 s (aldehyde C=O), 1778 s (lactone C=O); MS Found: 311.1 (M+1), Calc. 310.16; Mp 57–57.5° C.

Allylic alcohol 22. Solid NaBH$_4$ (130 mg, 3.44 mmol) was added to a solution of aldehyde 21 (536 mg, 1.73 mmol) in CH$_2$Cl$_2$ (28 mL) stirring at −78° C., followed by slow addition of methanol (12 mL). The mixture was allowed to warm slowly to RT and then quenched by careful addition of saturated aqueous NH$_4$Cl (5 mL), then diluted with water, and extracted 3 times with CH$_2$Cl$_2$. The organic extract was washed once with brine, dried over Na$_2$SO$_4$ and rotary evaporated. The resulting colorless oil contained 1% of CH$_2$Cl$_2$ by $^1$H NMR, but otherwise was completely pure (593 mg, quant. yield). The oil crystallized after prolonged standing. $^1$H NMR (CDCl$_3$, D$_2$O, 500 MHz): δ 0.07 (s, 3H), 0.09 (s, 3H), 0.87 (s, 9H), 1.16 (s, 3H), 1.18 (s, 3H), 4.03 (d, J=8.7, 1H), 4.15 (d, J=14.0, 1H), 4.21 (d, J=8.7, 1H), 4.28 (d, J=14.0, 1H), 4.30 (d, J=0.8, 1H), 5.59 (d, J=0.8, 1H); $^{13}$C NMR (CDCl$_3$, 100 MHz): −5.1, −4.6, 16.3, 17.4, 18.0, 25.7, 54.6, 58.7, 59.5, 78.9, 83.1, 126.2, 150.6, 177.3; IR (NaCl, cm$^{-1}$): 1757 s (C=O), 3436 br (O—H); MS Found: 313.1 (M+1), Calc. 312.18; Mp 71.5–72.5° C.

Claisen Esters 23 and 24. A mixture of allylic alcohol 22 (593 mg, 1.87 mmol), pivalic acid (75 mg, 0.74 mmol), freshly distilled triethyl orthoacetate (5.5 mL, 30 mmol), and mesitylene (5.5 mL) was stirred in an oil bath at 135–140° C. in a flask equipped with a short-path distillation head under a slow flow of argon, adding 75 mg of pivalic acid every 2 hours and monitoring the progress of the reaction by $^1$H NMR. After 12 hrs, 2 mL of triethyl orthoacetate was added and the heating was continued overnight. NMR analysis indicated ca. 95% conversion. The mixture was cooled to RT, the solvents were removed by Kugelrohr distillation at 100° C., and the residue was purified by flash chromatography (hexanes/EtOAc 14:1) to afford 658 mg (92% yield) of the product as a mixture of diastereomers (23/24=1.8:1). $^1$H NMR (CDCl$_3$, 400 MHz): δ −0.03 (s, 1.65H), 0.08 (app s, 4.65H), 0.11 (s, 3H), 0.86 (s, 4.95H), 0.88 (s, 9H), 1.18 (s, 3H), 1.19 (s, 3H), 1.23–1.30 (m, 7.95H), 2.46 (dd, J=15.8, J=7.4, 1H), 2.53 (m, 1.1H), 2.58 (dd, J=15.8, J 6.5, 1H), 3.05 (m, 1H), 3.24 (m, 0.55H), 3.88 (d, J=8.7, 1H), 3.90 (d, J=4.1, 1H), 3.94 (d, J=8.2, 0.55H), 4.13–4.19 (m, 5.2H), 4.85 (d, J=3, 0.55H), 4.91 (d, J=3, 0.55H), 5.00 (d, J=2.2, 1H), 5.03 (d, J=2.2, 1H); IR (NaCl, cm$^{-1}$): 1736s (ester C=O), 1777 s (lactone C=O); MS Found: 383.2 (M+1), Calc. 382.22.

Iodolactones 25 and 26. Part A: Hydrolysis. The diastereomeric mixture of esters 23 and 24 (569 mg, 1.49 mmol) was stirred with a solution of LiOH (200 mg) in a mixture of MeOH (6 mL) and water (2 mL) at RT for 12 hrs, diluted with water, acidified with 1 M HCl to pH 2–3, and extracted 3 times with CH$_2$Cl$_2$. The organic extract was washed with brine, dried over Na$_2$SO$_4$, and rotary evaporated. The residue (ca. 0.55 g) was used directly in the next step. $^1$H NMR (CDCl$_3$, 400 MHz): δ 0.01 (s, 1.65H), 0.08 (s, 3H), 0.09 (s, 1.65H), 0.11 (s, 3H), 0.87 (s, 4.95H), 0.89 (s, 9H), 1.18 (s, 3H), 1.20 (s, 3H), 1.23 (s, 1.65H), 1.25 (s, 1.65H), 2.53 (dd, J=16.2, J=7.3, 1H), 2.61 (m, obscured by 2.64dd, 1.1H), 2.64 (dd, J=16.2, J=6.6, 1H), 3.06 (m, 1H), 3.23 (m, 0.55H), 3.88 (d, J=4.0, 1H), 3.89 (d, J=8.6, 1H), 3.95 (d, J=8.2, 0.55H), 4.15 (d, J=8.2, 0.55H), 4.16 (d, obscured by 4.19d, 0.55H), 4.19 (d, J=8.6, 1H), 4.90 (d, J=2.9, 0.55H), 4.95 (d, J=2.9, 0.55H), 5.04 (d, J=2.2, 1H), 5.06 (d, J=2.2, 1H), COOH not observed; IR (NaCl, cm$^{-1}$): 1711s (acid C=O), 1774s, br (lactone C=O), 3000–3500br (COO—H); MS Found: 355.1 (M+1), Calc. 354.19.

Part B: Iodolactonization. To a solution of the mixture of carboxylic acids 23a and 23b (0.55 g, see above) in 3 mL of THF, was added 7.5 mL of saturated aqueous NaHCO$_3$. The mixture was cooled in an ice bath, treated with a solution of I$_2$ (1.143 g, 4.5 mmol) in 12 mL of THF, protected from light, and stirred at RT for 12 hrs. Excess I$_2$ was quenched by addition of aqueous Na$_2$SO$_3$, the mixture was diluted with water and extracted 3 times with CH$_2$Cl$_2$. The organic extract was washed with brine, dried over Na$_2$SO$_4$, and rotary evaporated. The mixture of products crystallized spontaneously. The crude product was taken up in CH$_2$Cl$_2$ and preadsorbed on silica gel. Column chromatography (hexanes/EtOAc 7:1, then 3:1) gave incomplete separation. The mixed fractions were chromatographed again. Combined yield of the desired iodolactone 26 was 421 mg (59% based on the ester mixture). Additionally, 250 mg of the epimeric iodolactone 25 (35% yield) was obtained. 26 (major iodolactone): $^1$H NMR (CDCl$_3$, 400 MHz): δ 0.08 (app s, 6H), 0.89 (s, 9H), 1.17 (s, 3H), 1.24 (s, 3H), 2.45 (dd, J=19.3, J=2.4, 1H), 2.79 (dd, J=11.5, J=2.4, 1H), 3.33 (d, J=11.1, 1H), 3.36 (dd, partly obscured by 3.33d, J=19.3, J=11.5, 1H), 3.57 (d, J=11.1, 1H), 3.82 (s, 1H), 3.89 (d, J=8.4, 1H), 4.31 (d, J=8.4, 1H); $^{13}$C NMR (CDCl$_3$, 100 MHz): −5.3, −4.9, 7.8, 15.8, 16.2, 17.7, 25.6, 37.3, 55.9, 57.1, 61.2, 72.4, 87.9, 95.5, 174.1, 176.3; IR (NaCl, cm$^{-1}$): 1777s (C=O); MS Found: 481.0 (M+1), Calc. 480.08; Mp 213–214° C. 25 (minor iodolactone): $^1$H NMR (CDCl$_3$, 400 MHz): δ 0.06 (s, 3H), 0.10 (s, 3H), 0.91 (s, 9H), 1.20 (s, 3H), 1.23 (s, 3H), 2.78–2.89 (m, 2H), 3.06 (m, 1H), 3.25 (d, J=11.1, 1H), 3.73 (d, J=11.1, 1H), 3.85 (d, J=9.4, 1H), 4.00 (d, J=7.2, 1H), 4.27 (d, J=9.4, 1H); $^{13}$C NMR (CDCl$_3$, 100 MHz): −5.0, −4.5, 14.5, 15.7, 17.2, 17.8, 25.7, 30.9, 50.0, 55.9, 61.3, 73.7, 78.3, 93.4, 175.4, 176.0; IR (NaCl, cm$^{-1}$): 1774s (C=O); MS Found: 481.0 (M+1), Calc. 480.08; Mp 216–217° C.

Keck Product 27. Iodolactone 26 (421 mg, 0.876 mmol), allyltributyltin (1.36 mL, 4.39 mmol), AIBN (14 mg, 0.085 mmol), and benzene (4.4 mL) were added into a flask equipped with a reflux condenser and a magnetic stirring bar, the mixture was degassed using the freeze-pump-thaw technique (3–4 cycles) and immersed into an oil bath kept at 85° C. After 3 hours, another 14 mg of AIBN was added, and the heating was continued for an additional 1.5 hours. The mixture was cooled, the solvent was rotary evaporated, and the residue was diluted with 1 mL of CH$_2$Cl$_2$ (to prevent crystallization) and chromatographed (hexanes/EtOAc 7:1) to afford the crystalline product contaminated with Bu$_3$SnBr. The impurities were removed by washing the crystals with hexanes, evaporating the washings, and washing the crystalline residue with hexanes again, and so on until evaporation gave mostly oil. The pure product thus obtained weighed 258 mg (75% yield). $^1$H NMR (CDCl$_3$, 500 MHz): δ 0.06 (s, 3H), 0.07 (s, 3H), 0.88 (s, 9H), 1.17 (s, 3H), 1.23 (s, 3H), 1.56 (m, 1H), 1.98 (m, 1H), 2.05 (m, 1H), 2.17 (m, 1H), 2.54 (dd, J=8.8, J=1.5, 1H), 2.71 (d, J=10.9, 1H), 3.00 (dd, J=18.8, J=10.9, 1H), 3.78 (s, 1H), 3.87 (d, J=8.6, 1H), 4.21 (d, J=8.6, 1H), 5.05 (d, J=10.2, 1H), 5.10 (dd, J=17.2, J=1.2, 1H), 5.77 (d, J=10.3, 1H), 5.80 (m, 1H); $^{13}$C NMR (CDCl$_3$, 100 MHz): −5.2, −4.8, 16.2, 16.4, 17.8, 25.6, 27.7, 33.9, 36.5, 54.0, 58.0, 60.3, 72.5, 89.0, 98.3, 116.1, 136.5, 174.6, 176.6; IR (NaCl, cm$^{-1}$): 1779s (C=O); MS Found: 395.2 (M+1), Calc. 394.22; Mp 154–155° C.

Cyclization Precursor 29. To a solution of 27 (258 mg, 0.654 mmol) in 12 mL of THF stirring at −78° C. was added LHMDS (1 M in THF, 0.75 mL). After 0.5 hour, TMSCl (100 μL, 0.788 mmol) was added. The mixture was stirred for 0.5 hour at −78° C., then for 0.5 hour at RT, cooled to −78° C. and treated with PhSeCl (142 mg, 0.741 mmol) in 9 mL of THF. The mixture was allowed to warm to RT over 1.5 hours, diluted with water, and extracted with Et$_2$O 3 times. The ethereal extract was dried over MgSO$_4$, rotary evaporated, the residue was diluted with CH$_2$Cl$_2$, and evaporated again. The crude selenide was dissolved in 7 mL of dry MeCN and treated with a solution of PhSeBr until brownish color persisted (ca. 6 mL of solution prepared from 119 mg of (PhSe)$_2$, 0.38 mL of 2M Br$_2$ in CHCl$_3$, and 6.6 mL of MeCN) at RT. After 0.5 hour, the mixture was evaporated at 25° C. by stirring under vacuum, the residue redissolved in 20 ml of CH$_2$Cl$_2$, and ozonated at −78° C. until blue color persisted. The cold mixture was treated with 3 mL of 1-hexene and then added in several portions to a boiling solution of 2 mL of NEt$_3$ in 80 mL of benzene. After the addition was complete, the mixture was refluxed for 0.5 hour, evaporated to dryness, and the residue was chromatographed (hexanes/EtOAc 4:1) to afford 237 mg (77% yield) of the white crystalline product. $^1$H NMR (CDCl$_3$, 400 MHz): δ 0.17(s, 3H), 0.19 (s, 3H), 0.90 (s, 9H), 0.91 (s, 3H), 1.20 (s, 3H), 2.18–2.26 (m, 1H), 2.32–2.49 (m, 3H), 3.93 (d, J=10.2, 1H), 4.36 (s, 1H), 4.68 (d, J=10.2, 1H), 5.42 (d, J=2.0, 1H), 5.57 (dd, J=1.0, J=0.8, 1H), 5.93 (s, 1H); $^{13}$C NMR (CDCl$_3$, 100 MHz): −5.2, −5.0, 16.2, 18.4, 25.8, 32.4, 35.5, 49.7, 59.7, 71.7, 73.9, 94.7, 114.3, 117.4, 132.1, 171.4, 171.9, 175.6; IR (NaCl, cm$^{-1}$): 1765s (C=O); MS Found: 471.0 (M+1), Calc. 470.11; Mp 145–146.5° C.

Exo Olefin 30. A solution of 29 (237 mg, 0.492 mmol), Bu$_3$SnH (270 μL, 0.985 mmol), and AIBN (8 mg, 0.049 mmol) in 50 mL of benzene was degassed using the freeze-pump-thaw technique (3 cycles) and heated under reflux in an oil bath at 85° C. After 2.5 hrs, 8 mg of AIBN was added and the heating was continued for 1.5 hrs. The mixture was evaporated, and the residue was chromatographed (hexanes/EtOAc 7:1) to afford 185 mg of the white crystalline product still containing tributyltin impurities. The latter were removed by washing the crystals with hexanes (3×3 mL), evaporating the washings, and washing the crystalline residue with hexanes again, and so on until evaporation gave mostly oil. The product thus obtained was pure by $^1$H NMR and weighed 177 mg (90% yield). $^1$H NMR (CDCl$_3$, 400 MHz): δ 0.01(s, 3H), 0.06 (s, 3H), 0.86 (s, 9H), 1.22 (s, 3H), 1.24 (s, 3H), 1.76 (m, 1H), 2.14 (m, 1H), 2.61 (m, 2H), 2.79 (d, J=19.2, 1H), 3.03 (d, J=19.2, 1H), 3.89 (d, J=8.4, 1H), 4.01 (s, 1H), 4.43 (d, J=8.4, 1H), 4.95 (app s, 1H), 5.25 (dd, J=1.9, J=1.7, 1H); $^{13}$C NMR (CDCl$_3$, 100 MHz): −4.4, −3.4, 16.7, 17.7, 17.9, 25.8, 33.8, 37.6, 43.6, 56.8, 62.5, 66.3, 72.4, 89.2, 106.2, 112.2, 152.9, 174.5, 177.0; IR (NaCl, cm$^{-1}$): 1778 s (C=O); MS Found: 393.1 (M+1), Calc. 392.20; Mp 175–175.5° C.

Alcohol 31. A mixture of 30 (177 mg, 0.451 mmol), TsOH.H$_2$O (343 mg, 1.80 mmol), and benzene (17 mL) was heated under reflux for 3 hours in an oil bath at 90° C., then cooled, diluted with Et$_2$O, and washed with aqueous NaHCO$_3$. The aqueous wash was extracted with CH$_2$Cl$_2$ 3 times, the combined organic phase was dried over Na$_2$SO$_4$, rotary evaporated, and chromatographed (CH$_2$Cl$_2$/EtOAc 5:1) to afford 123 mg (98%) of the product. $^1$H NMR (CDCl$_3$, 300 MHz): δ 1.19 (s, 3H), 1.23 (s, 3H), 1.82 (d, J=1.5, 3H), 1.82 (m, 2H), 2.66 (d, J=19.1, 1H), 2.85 (d, J=19.1, 1H), 3.75 (d, J=6.0, 1H), 3.95 (d, J=8.7, 1H), 4.16 (d, J=6.0, 1H), 4.22 (d, J=8.7, 1H), 5.37 (m, J=32 1.5, 1H), $^{13}$C NMR (CDCl$_3$, 75 MHz): 15.0, 15.7, 16.7, 39.9, 41.0, 55.5, 62.5, 69.8, 73.8, 86.3, 104.6, 124.6, 141.5, 175.4, 179.0; $^1$H NMR (CD$_3$OD, 400 MHz): 1.15 (s, 3H), 1.19 (d, J=0.8, 3H), 1.79 (ddd, J=2.4, J=2.1, J=1.5, 3H), 2.35 (ddq, J=18.4, J=2.4, J=2.4, 1H), 2.55 (ddq, J=18.4, J=2.1, J=2.1, 1H), 2.77 (d, J=19.3, 1H), 2.87 (d, J=19.3, 1H), 3.97 (d, J=8.6, 1H), 4.08 (s, 1H), 4.16 (d, J=8.6, J=0.8, 1H), 5.33 (ddq, J=2.4, J=2.1, J=1.5, 1H); 67 $^{13}$C NMR (CD$_3$OD, 100 MHz): 15.1, 16.1, 16.9, 40.6, 41.9, 57.0, 64.0, 71.5, 74.4, 87.1, 106.5, 125.1, 143.8, 177.9, 180.2; IR (NaCl, cm$^{-1}$): 1770 s (C=O), 3462 br (O—H); MS Found: 279.1 (M+1), Calc. 278.12; Mp 189–190° C. (softens at 175° C).

Our $^1$H and $^{13}$C NMR data for spectra recorded in CD$_3$OD match those reported by Fukuyama et al.[5b] for CDCl$_3$ (probably due to a typographical error).

Epoxides 2 and 2a. The procedure of Fukuyama et al.[5b] was essentially followed. A solution of alcohol 30 (123 mg, 0.442 mmol) and mCPBA (180 mg, 1.04 mmol) in 12 ml of CH$_2$Cl$_2$ was left for 2 days at RT. The mixture was treated with saturated aqueous Na$_2$SO$_3$ and aqueous NaHCO$_3$, and extracted 3 times with CH$_2$Cl$_2$. The extract was washed with brine, dried over Na$_2$SO$_4$, and rotary evaporated. The crude product (133 mg, quant.) consisted of a 3.5:1 mixture of epoxides 2 and 2a. The mixture was used directly in the next step, since column chromatography (CHCl$_3$/MeOH[5b] or CH$_2$Cl$_2$/AcOEt) did not result in efficient separation of the epimers. The pure major epoxide 2 could be obtained by two recrystallizations from EtOAc/hexanes. Major epoxide 2: $^1$H NMR (CD$_3$OD, 400 MHz): δ 1.11 (s, 3H), 1.16 (s, 3H), 1.54 (s, 3H), 2.07 (d, J=16.2, 1H), 2.25 (dd, J=16.2, J=1.6, 1H), 2.58 (d, J=19.1, 1H), 3.00 (d, J=19.1, 1H), 3.66 (d, J=1.6, 1H), 3.93 (d, J=8.5, 1H), 4.12 (s, 1H), 4.47 (d, J=8.5, 1H); $^{13}$C NMR (CD$_3$OD, 100 MHz): 16.1, 16.6, 17.9, 37.3, 38.6, 57.3, 64.8, 67.4, 69.4, 71.7, 75.8, 83.9, 108.3, 177.4, 180.2; IR (NaCl, cm$^{-1}$): 1772 s (C=O), 3410 br (O—H); MS Found: 295.0 (M+1), Calc. 294.11; Mp 249.5–250° C.

(±)-Merrilactone A (1). The procedure of Fukuyama et al.[5b] was essentially followed. The mixture of epoxides 2 and 2a (133 mg) was stirred with TsOH.H$_2$O (80 mg, 0.42 mmol) in 25 mL of CH$_2$Cl$_2$ for 1 day at RT. The TsOH.H$_2$O was filtered off and washed 3 times with CH$_2$Cl$_2$. The crude product was adsorbed on silica gel (ca. 0.5 g) and chromatographed (CH$_2$Cl$_2$/AcOEt 4:1, then 2:1, then 1:1) to give 14 mg (11% from alcohol 30) of somewhat impure minor epoxide 2a followed by (±)-merrilactone A (92 mg, 71% from alcohol 30). Minor epoxide 2a: $^1$H NMR (CD$_3$OD, 300 MHz): δ 1.10 (s, 3H), 1.13 (d, J=0.7, 3H), 1.49 (s, 3H), 1.93 (dd, J=16.2, J=2.2, 1H), 2.39 (d, J=16.2, 1H), 2.82 (d, j=19.0, 1H), 3.28 (d, J=19.0, 1H), 3.40 (d, J=2.2, 1H), 3.74 (d, J=9.0, 1H), 4.14 (s, 1H), 5.20 (d, J=9.0, 1H); $^{13}$C NMR (CD$_3$OD, 75 MHz): 16.0, 17.0, 17.8, 37.4, 41.7, 64.2, 65.5, 68.0, 73.4, 88.0, 107.4, 176.6, 180.2; IR (NaCl, cm$^{-1}$): 1772 s (C=O), 3450 br (O—H); MS Found: 295.0 (M+1), Calc. 294.11; Merrilactone A: $^1$H NMR (CD$_3$OD, 400 MHz): δ 1.08 (s, 3H), 1.23 (s, 3H), 1.48 (s, 3H), 2.28 (dd, J=15.4, J=1.5, 1H), 2.68 (d, J=19.4, 1H), 2.70 (d, J=5.2, 1H), 2.73 (d, J=5.2, 1H), 2.90 (d, J=19.4, 1H), 3.94 (dd, J=5.2, J=1.5, 1H), 4.01 (d, J=10.1, 1H), 4.59 (d, J=10.1, 1H), 4.73 (s, 1H); $^{13}$C NMR (CD$_3$OD, 75 MHz): 16.0, 17.4, 17.4, 32.2, 43.9, 58.5, 61.2, 66.0, 75.5, 79.9, 90.3, 96.2, 107.3, 177.7, 179.3; IR (NaCl, cm$^{-1}$): 1761 s (C=O), 3450 br (O—H); MS Found: 295.0 (M+1), Calc. 294.11; Mp 233.5–234.5° C. (from EtOAc/CHCl$_3$).

Example 2

The schemes above have been adapted to synthesizing nitrogen containing Merrilactone analogues having the general structure:

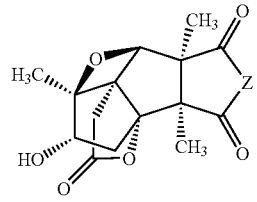

wherein Z is >N—X, where X is straight or branched substituted or unsubstituted alkyl, alkenyl or alkynyl, or cycloalkyl, aryl, heterocycloalkyl, heteroaryl, aralkyl, amino, alkyl amino, or dialkyl amino.

The basic modification which resulted in such analogues was simply the replacing of the starting material

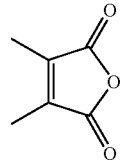

with a nitrogen containing starting material such as

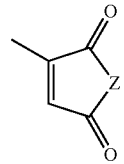

and alkylating, e.g. methylating, the resulting Diels-Alder adduct.

REFERENCES (1) Hefti, F. *Annu. Rev. Pharmacol. Toxicol.* 1997, 37, 239.
(2) (a) Siegel, G. J.; Chauhan, N. B. *Brain Res. Rev.* 2000, 33, 199; (b) Gash, D. M.; Zhang, Z.; Ovadia, A.; Cass, W.

A.; Yi, A.; Simmerman, L.; Russel, D.; Martin, D.; Lapchak, P. A.; Collins, F.; Hoffer, B. J.; Gerhardt, G. A. *Nature,* 1996, 380, 252.
(3) Backman, C.; Rose, G. M.; Hoffer, B. J.; Henry, M. A.; Bartus, R. T.; Friden, P.; Granholm, A. C. *J. Neurosci.* 1996, 16, 5437.
(4) For a discussion of small molecule mimetics and for references to neurotrophic natural products, see: Ref.1, pp. 255–257.
(5) (a) Huang, J.-m.; Yokoyama, R.; Yang, C.-s.; Fukuyama, Y. *Tetrahedron Lett.* 2000, 41, 6111 (b) Huang, J.-m.; Yang, C.-s.; Tanaka, M.; Fukuyama, Y. *Tetrahedron* 2001, 57, 4691.
(6) (a) Marinovic, N. N.; Ramanathan, H. *Tetrahedron Lett.* 1983, 24, 1871; (b) Jasperse, C. P.; Curran, D. P.; Fevig, T. L. *Chem. Rev.* 1991, 91, 1237.
(7) DMMA itself is capable of reacting only with the most reactive dienes: (a) Dauben, W. G.; Kessel, C. R.; Takemura, K. H. *J. Am. Chem. Soc.* 1980, 102, 6893 and references cited therein; (b) Rae, I. D.; Serelis, A. K.; *Aust. J. Chem.* 1990, 43, 1941; (c) von Ziegler, K.; Flaig, W.; and Velling, G. *Liebigs Ann.* 1950, 567, 204.
(8) Defoin, A.; Pires, J.; Streith, J. *Helv. Chim. Acta* 1991, 74, 1665.
(9) (a) Soai, K.; Yokoyama, S.; Mochida, K. *Synthesis* 1987, 647; (b) Alexandre, F.-R.; Legoupy, S.; Huet, F. *Tetrahedron* 2000, 56, 3921.
(10) Pangborn, A. B.; Giardello, M. A.; Grubbs, R. H.; Rosen, R. K.; Timmers, F. J. *Organometallics* 1996, 15, 1518.
(11) Jaeschke, G.; Seebach, D. *J. Org. Chem.* 1998, 63, 1190.
(12) Corey, E. J.; Danheiser, R. L.; Chandrasekaran, S.; Siret, P.; Keck, G. E.; Gras, J. L. *J. Am. Chem. Soc.* 1978, 100, 8031.
(13) Ward, D. E.; Rhee, C. K. Can. *J. Chem.* 1989, 67, 1210.
(14) (a) Johnson, W. S.; Wertheman, L.; Bartlett, W. R.; Lee, T.-T.; Faulkner, D. J.; Petersen, M. R. *J. Am. Chem. Soc.* 1970, 92, 741; (b) Ziegler, F. E. *Acc. Chem. Res.* 1977, 10, 227.
(15) Keck, G. E.; Yates, J. B. *J. Am. Chem. Soc.* 1982, 104, 5829.
(16) (a) Rauscher, S. *Tetrahedron Lett.* 1977, 44, 3909.
(17) Henbest, H. B.; Wilson, R. A. L. *Chem. Ind.* (London) 1956, 659.

What is claimed is:

1. A composition comprising a racemate of a compound having the structure

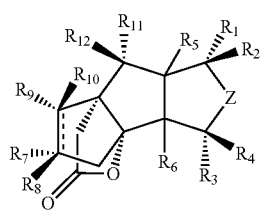

wherein Z is O or >N—X, where X is H, straight or branched substituted or unsubstituted alkyl, alkenyl or alkynyl, or acyl, carbamoyl, cycloalkyl, aryl, heterocycloalkyl, heteroaryl, aralkyl, amino, alkyl amino, or dialkyl amino;
wherein each of $R_1$ and $R_2$ is H or $R_1$ and $R_2$ together are =O;
wherein each of $R_3$ and $R_4$ is H or $R_3$ and $R_4$ together are =O;
wherein each of $R_5$ and $R_6$ is, independently, H, alkyl, aralkyl, or aryl;
wherein each of $R_7$ and $R_8$ is, independently, H, OH or $OR_{14}$,
where $R_{14}$ is alkyl or —C(O)—$R_{15}$,
where $R_{15}$ is H, —$CH_2R_{16}$, —$CHR_{16}R_{16}$, —$CR_{16}R_{17}R_{16}$, —$OR_{16}$, alkenyl or alkynyl, cycloalkyl, aryl, heterocycloalkyl, heteroaryl, aralkyl, amino, alkyl amino, or dialkyl amino,
wherein each $R_{16}$ is straight or branched, substituted or unsubstituted alkyl, alkenyl or alkynyl, cycloalkyl, aryl, heterocycloalkyl, heteroaryl, aralkyl, or amino; and
wherein $R_{17}$ is straight or branched, unsubstituted alkyl, alkenyl or alkynyl, cycloalkyl, aryl, heterocycloalkyl, heteroaryl, aralkyl, or amino,
or wherein $R_7$ and $R_9$ together are >O;
wherein each of $R_9$ and $R_{10}$ is, independently, H, alkyl, OH, or $OR_{13}$, where $R_{13}$ is an alkyl, an acyl, or an amide, or $R_9$ and $R_{10}$ together are =$CH_2$,
or wherein $R_8$ and $R_{10}$ together are >O;
wherein if one of $R_7$ or $R_8$ and one of $R_9$ or $R_{10}$ is absent, a double bond is formed as indicated by the broken line; and
wherein each of $R_{11}$ and $R_{12}$ is, independently, H, OH, or $OR_{13}$, where $R_{13}$ is an alkyl, an acyl, or an amide, or $R_{11}$ and $R_{12}$ together are =O,
or wherein $R_{12}$ and $R_{10}$ together are >O.

2. The composition of claim 1, wherein Z is >N—X, where X is H, straight or branched substituted or unsubstituted alkyl, alkenyl or alkynyl, or acyl, carbamoyl, cycloalkyl, aryl, heterocycloalkyl, heteroaryl, aralkyl, amino, alkyl amino, or dialkyl amino.

3. The composition of claim 1, wherein Z is O or >N—X, where X is H, straight or branched alkyl, alkenyl or alkynyl, or acyl, carbamoyl, cycloalkyl, aryl, heterocycloalkyl, heteroaryl, aralkyl, amino, alkyl amino, or dialkyl amino;
wherein each of $R_1$ and $R_2$ is H or $R_1$ and $R_2$ together are =O;
wherein each of $R_3$ and $R_4$ is H or $R_3$ and $R_4$ together are =O;
wherein each of $R_5$ and $R_6$ is, independently, H, alkyl, or aralkyl;
wherein each of $R_7$ and $R_8$ is, independently, H or $OR_{14}$, where $R_{14}$ is alkyl or —C(O)—$R_{15}$,
where $R_{15}$ is H, —$CH_2R_{16}$, —$CHR_{16}R_{16}$, —$CR_{16}R_{17}R_{16}$, —$OR_{16}$, cycloalkyl, aryl, or aralkyl,
wherein each $R_{16}$ is alkyl, cycloalkyl, or aryl, aralkyl; and
wherein $R_{17}$ is alkyl, cycloalkyl, aryl, or aralkyl,
or wherein $R_7$ and $R_9$ together are >O;
wherein each of $R_9$ and $R_{10}$ is, independently, H, alkyl, OH, or $OR_{13}$, where $R_{13}$ is an alkyl, an acyl, or an amide, or $R_9$ and $R_{10}$ together are =$CH_2$,
or wherein $R_8$ and $R_{10}$ together are >O;
wherein if one of $R_7$ or $R_8$ and one of $R_9$ or $R_{10}$ is absent, a double bond is formed as indicated by the broken line; and
wherein each of $R_{11}$ and $R_{12}$ is, independently, H, OH, or $OR_{13}$, where $R_{13}$ is an alkyl, an acyl, or an amide, or $R_{11}$ and $R_{12}$ together are =O,
or wherein $R_{12}$ and $R_{10}$ together are >O.

4. The composition of claim 1 having the structure

31

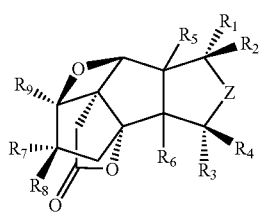

wherein Z is >O;
wherein each of $R_1$ and $R_2$ is H, or $R_1$ and $R_2$ together are =O;
wherein each of $R_3$ and $R_4$ is H, or $R_3$ and $R_4$ together are =O;
wherein each of $R_5$ and $R_6$ is, independently, H, alkyl, aralkyl, or aryl;
wherein each of $R_7$ and $R_8$ is, independently, H or $OR_{14}$, where $R_{14}$ is alkyl or —C(O)—$R_{15}$,
where $R_{15}$ is H, —$CH_2R_{16}$, —$CHR_{16}R_{16}$, —$CR_{16}R_{17}R_{16}$, —$OR_{16}$, alkenyl or alkynyl, cycloalkyl, aryl, heterocycloalkyl, heteroaryl, aralkyl, amino, alkyl amino, or dialkyl amino,
wherein each $R_{16}$ is straight or branched, substituted or unsubstituted alkyl, alkenyl or alkynyl, cycloalkyl, aryl, heterocycloalkyl, heteroaryl, aralkyl, or amino; and
wherein $R_{17}$ is straight or branched, unsubstituted alkyl, alkenyl or alkynyl, cycloalkyl, aryl, heterocycloalkyl, heteroaryl, aralkyl, or amino; and
wherein $R_9$ is H, alkyl, OH, or $OR_{13}$, where $R_{13}$ is an alkyl, an acyl, or an amide.

5. The composition of claim 4, wherein $R_9$ is H, alkyl or $OR_{13}$, where $R_{13}$ is an alkyl, an acyl, or an amide.

6. The composition of claim 4,
wherein $R_1$ and $R_2$ together are =O;
wherein each of $R_3$ and $R_4$ is H;
wherein each of $R_5$ and $R_6$ is, independently, H, alkyl, or aralkyl;
wherein each of $R_7$ and $R_8$ is, independently, H or $OR_{14}$, where $R_{14}$ is alkyl or —C(O)—$R_{15}$,
where $R_{15}$ is H, —$CH_2R_{16}$, —$CHR_{16}R_{16}$, —$CR_{16}R_{17}R_{16}$, —$OR_{16}$, alkenyl or alkynyl, cycloalkyl, aryl, heterocycloalkyl, heteroaryl, aralkyl, amino, alkyl amino, or dialkyl amino,
wherein each $R_{16}$ is straight or branched, substituted or unsubstituted alkyl, alkenyl or alkynyl, cycloalkyl, aryl, heterocycloalkyl, heteroaryl, aralkyl, or amino; and
wherein $R_{17}$ is straight or branched, unsubstituted alkyl, alkenyl or alkynyl, cycloalkyl, aryl, heterocycloalkyl, heteroaryl, aralkyl, or amino; and
wherein $R_9$ is alkyl.

7. The composition of claim 1, wherein the compound is:

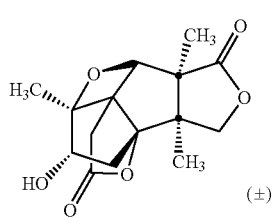
(±)

32

8. A process for preparing the compound of the composition of claim 7 comprising:
a) reacting a compound having the structure

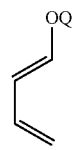

where Q is a silyl protecting group, with a compound having the structure

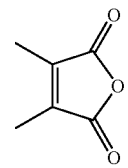

at a temperature of from about 140° C. to 230° C. to produce a compound having the structure

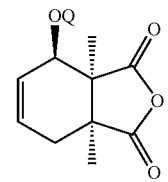

b) reacting the compound of step a) with MeONa to produce

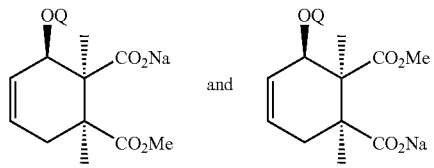

c) treating both products of step b) with $ClCO_2Me$ to produce

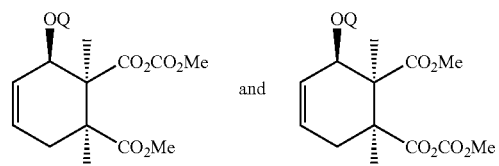

d) treating both products of step c) with $NaBH_4$ to produce

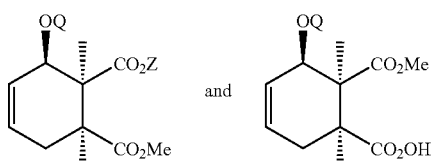

Z = CO₂Me; or Z = H e) treating the products of step d) with LiOH to produce

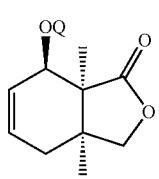

f) treating the product of step e) with O₃ followed by Bn₂NH*TFA to produce

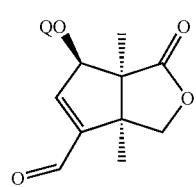

g) treating the product of step f) with NaBH₄ to produce

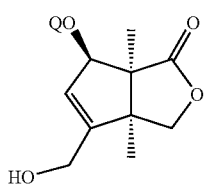

h) treating the product of step g) with MeC(OEt)₃ to produce

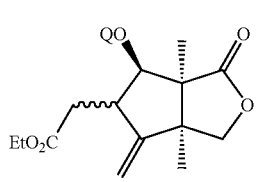

i) treating the product of step h) LiOH and I₂ and to produce

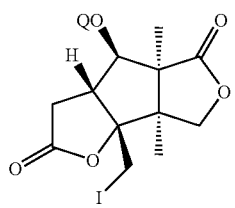

j) treating the product of step i) with allylSnBu₃ to produce

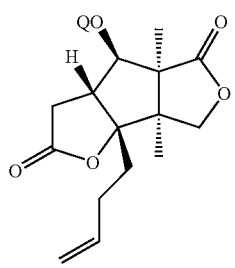

k) treating the product of step j) with LHMDS, TMSCl and PhSeCl, and then with PhSeBr and MeCN to produce

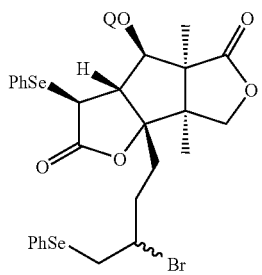

l) treating the product of step k) with O₃, CH₂Cl₂ and 1-hexene to produce

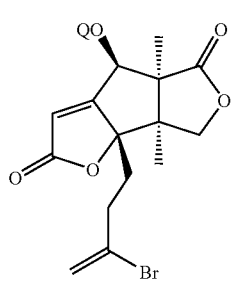

m) treating the product of step l) with Bu₃SnH and AIBN to produce n) treating the product of step m) with TsOH to produce

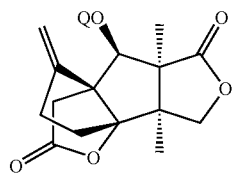

o) treating the product of step n) with mCPBA or a dimethyldioxirane to produce

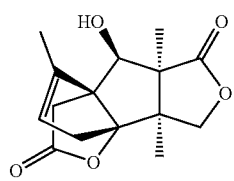

p) treating the product of step o) with an acid to produce the compound of the composition.

9. A process for preparing the compound of the composition of claim 7 comprising:

a) reacting a compound having the structure

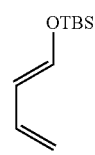

with a compound having the structure

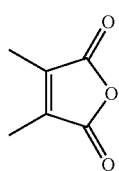

at a temperature of from about 160° C. to 180° C. to produce a compound having the structure

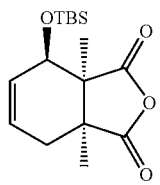

b) reacting the compound of step a) with MeONa and MeOH to produce

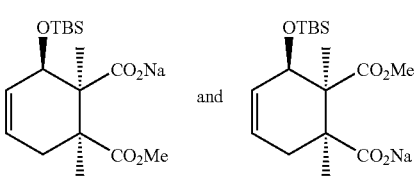

c) treating both products of step b) with ClCO₂Me in THF to produce

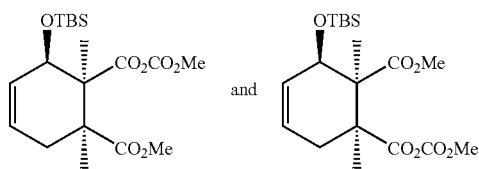

d) treating both products of step c) with NaBH₄ and MeOH to produce

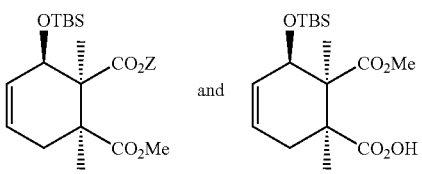

Z = CO₂Me; or Z = H e) treating the products of step d) with aqueous LiOH to produce

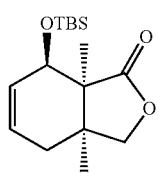

f) treating the product of step e) first with O₃ and PPh₃, and then with Bn₂NH*TFA in benzene to produce

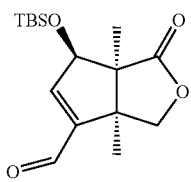

g) treating the product of step f) with NaBH₄ and CH₂Cl₂ in MeOH to produce

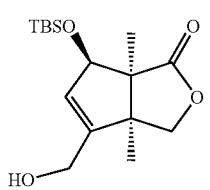

h) treating the product of step g) with MeC(OEt)₃ and PivOH to produce

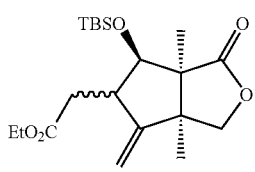

i) treating the product of step h) first with aqueous LiOH and MeOH, and then with I₂ and NaHCO₃ in THF to produce

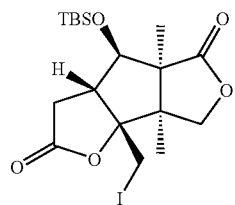

j) treating the product of step i) with allylSnBu₃, AIBN and PhH to produce

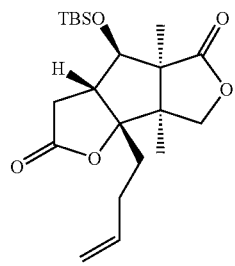

k) treating the product of step j) first with LHMDS, TMSCl and PhSeCl, and then with PhSeBr and MeCN to produce

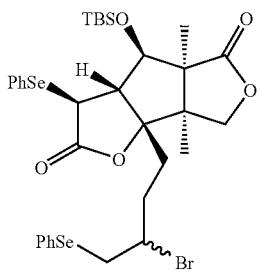

l) treating the product of step k) first with O₃, CH₂Cl₂ and 1-hexene, and then with PhH, NEt₃ under reflux conditions to produce

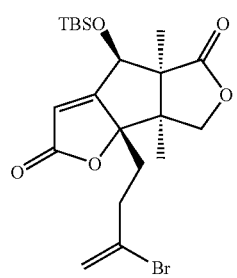

m) treating the product of step l) with Bu₃SnH and AIBN, and PhH to produce

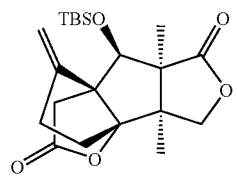

n) treating the product of step m) with aqueous TsOH and PhH under reflux conditions to produce

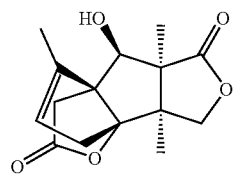

o) treating the product of step n) with mCPBA and CH₂Cl₂ to produce

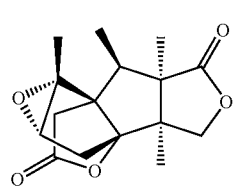

p) treating the product of step o) with aqueous TsOH and CH$_2$Cl$_2$ to produce the compound of the composition.

* * * * *